United States Patent
Che et al.

(10) Patent No.: US 6,858,747 B2
(45) Date of Patent: Feb. 22, 2005

(54) PROCESS TO PREPARE, 1,4-DIHYDROPYRIDINE INTERMEDIATES AND DERIVATIVES THEREOF

(75) Inventors: Daqing Che, Brantford (CA); Bhaskar Reddy Guntoori, Brantford (CA); K. S. Keshava Murthy, Ancaster (CA)

(73) Assignee: Apotex Pharmachem Inc., Brantford (CA)

(*) Notice: Subject to any disclaimer, the term of this patent is extended or adjusted under 35 U.S.C. 154(b) by 0 days.

(21) Appl. No.: 10/819,910

(22) Filed: Apr. 8, 2004

(65) Prior Publication Data

US 2004/0204604 A1 Oct. 14, 2004

(30) Foreign Application Priority Data

Apr. 14, 2003 (CA) ............................................. 2425561

(51) Int. Cl.[7] .................... C07C 69/79; C07C 205/00
(52) U.S. Cl. ............................. 560/53; 560/21; 560/51; 546/249; 546/321
(58) Field of Search ............................. 560/23, 51, 53; 546/249, 321

(56) References Cited

U.S. PATENT DOCUMENTS

| | | |
|---|---|---|
| 4,600,778 A | 7/1986 | Teller et al. ................ 546/249 |
| 5,310,917 A | 5/1994 | Auerbach ................... 540/249 |
| 5,977,369 A | 11/1999 | Desai et al. ................. 546/321 |

FOREIGN PATENT DOCUMENTS

| | | | |
|---|---|---|---|
| ES | 549753 | 12/1985 | |
| WO | WO 98/07698 | 7/1997 | ......... C07D/211/90 |

OTHER PUBLICATIONS

Cope, Arthur C., *Condensation Reactions. I. The Condensation of Ketones with Cyanoacetic Esters and the Mechanism of the Knoevenagel Reaction*, Journal of the American Chemical Society, 1937, vol. 59, pp. 2327–2330.

Fener, Chen et al., *Synthesis of Calcium Antagonist. III. Synthesis of Felodipine*, 1995, vol. 7, No. 2, pp. 154–157.

*Primary Examiner*—Paul J. Killos
(74) *Attorney, Agent, or Firm*—Kitt Sinden; Ivor M. Hughes; Marcelo K. Sarkis

(57) ABSTRACT

An improved catalyst is disclosed for a process involving the preparation of benzylidene intermediates useful in the preparation of 1,4-dihydropyridine compounds and derivatives thereof useful as medicines such as for example felodipine. This is accomplished by the condensation of an aldehyde and an acetoacetate in the presence of a novel catalyst system that includes a pyridyl carboxylic acid and a secondary amine. It has been found that through the use of the present invention the purity and yield of the desired isomer of the benzylidene intermediate can be maximized, thus avoiding the requirement of additional purification steps. The use of these intermediates can then be further reacted to form the required dihydropyridines, again having a very high purity and yield compared with the prior art.

21 Claims, No Drawings

PROCESS TO PREPARE, 1,4-DIHYDROPYRIDINE INTERMEDIATES AND DERIVATIVES THEREOF

FIELD OF THE INVENTION

This invention relates generally to the preparation of intermediates useful in the preparation of 1,4-dihydropyridines and derivatives thereof, more particularly to the preparation of intermediates useful in the preparation of felodipine and nitrendipine.

BACKGROUND OF THE INVENTION

Felodipine and nitrendipine, 1 and 2, represent effective medicines useful for the treatment of hypertension and as muscle relaxant drugs. They belong to a class of medicines collectively known as dihydropyridines.

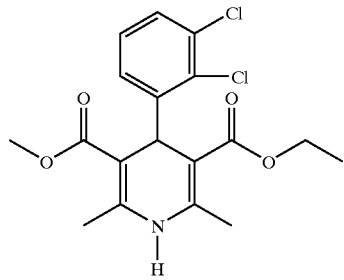

1

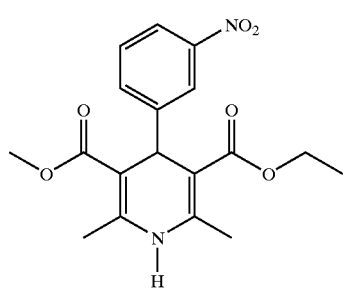

2

The preparation of felodipine (ethyl methyl 4-(2,3-dichlorophenyl)-1,4-dihydro-2,6-dimethyl-3,5-pyridine dicarboxylate) and related compounds typically involves a multistep protocol as depicted in Scheme 1.

Scheme 1

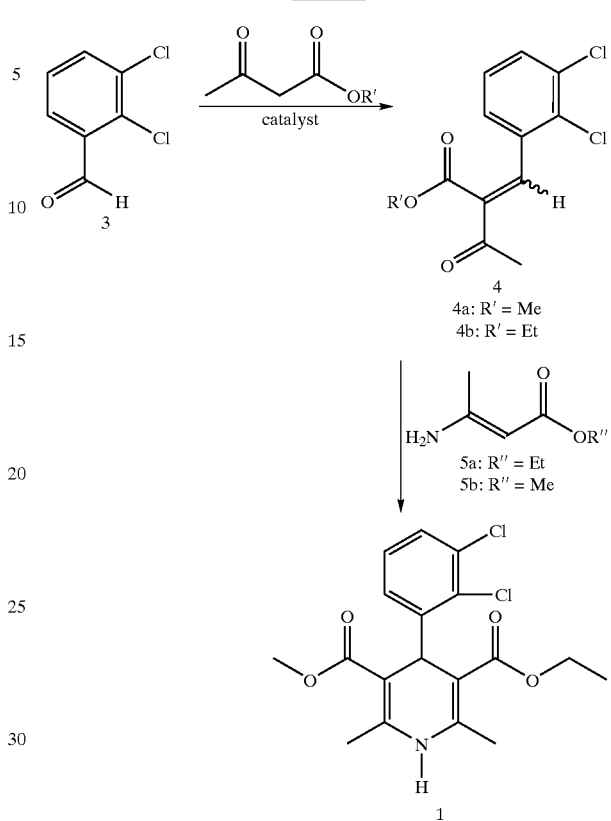

4
4a: R' = Me
4b: R' = Et

5a: R'' = Et
5b: R'' = Me

1

The acidic- and base-catalyzed condensation of benzaldehyde with an alkyl acetoacetate to form a key benzylidene intermediate of formula 4 is known. However, it is also well understood in the art that the performance of this condensation is very sensitive to the chemical nature of both base and acid. In particular, when basic catalysis is used, the benzylidene can be formed at a low temperature, but then reacts further with another molecule of the alkyl acetoacetate to form the bis-adduct (6, Scheme 2) as an impurity. This disadvantage is further compounded for the intermediate used in the preparation of felodipine since the requisite benzaldehyde component is 2,3-dichlorobenzaldehyde. When the resulting dihydropyridine molecule is made in the presence of these impurities, the chlorine atoms on the aromatic ring make the carbon atom of the aldehyde more electron deficient relative to benzaldehyde, further favouring the formation of the undesired bis-adduct 6. When acid is used as catalyst for this condensation, for instance as described in U.S. Pat. No. 5,310,917, a mixture of aldol by-products can also be formed.

Scheme 2

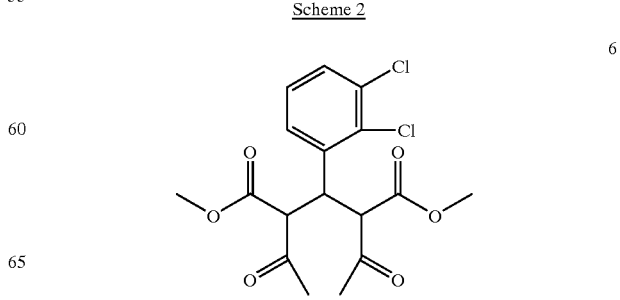

6

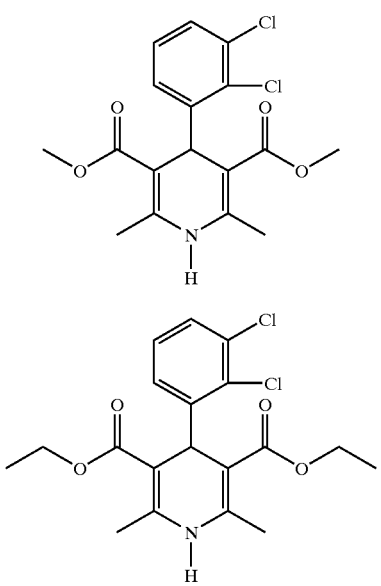

The use of piperidinium acetate as catalyst by Arthur C. Cope (Journal of the American Chemical Society, 1937, 59, 2327–2330) represents a landmark for making benzylidene compounds. For example, U.S. Pat. No. 4,600,778 disclosed a process for making nitrendipine and felodipine using this catalytic system in an alcoholic solvent. Novel catalytic systems, which purportedly overcome some of the deficiencies in the synthetic procedures disclosed in U.S. Pat. No. 4,600,778, are described in U.S. Pat. No. 5,977,369. However, although the benzylidene intermediate could be obtained as a mixture composed of two isomers, the yield still was only about 60% thereby making it undesirable for commercial production. Summarizing, the major disadvantages with the disclosed processes for the preparation of dihydropyridine compounds, particularly felodipine, from benzylidene intermediate processes of the prior art, include:

1. Formation of symmetrical diesters (dimethyl and diethyl, 7 and 8, respectively, Scheme 2) byproducts, which are very difficult to remove from the product.
2. Extractive workup for isolation of the desired product.
3. Purification by recrystallization requiring increased manufacturing time and solvent costs.
4. Low overall yield.

Therefore, a catalytic system combining an optimal balance of base and acid properties, which would provide the benzylidine intermediates in high yield and with a minimum number of side-products, was required.

It is accordingly an objective of the present invention to provide such a novel, simple and efficient process for the manufacture of benzylidene intermediates useful in the preparation of dihydropyridine compounds and, such as the dihydropyridine molecule, felodipine that overcomes the deficiencies in the prior art.

SUMMARY OF THE INVENTION

The present invention relates broadly to the preparation of benzylidene intermediates useful in the preparation of dihydropyridine compounds and derivatives thereof, and also the use of the intermediates formed by the process of the present invention to prepare dihydropyridine compounds useful as medicines.

In the broadest sense it is an object of the invention to provide for a process for the manufacture of a benzylidene intermediate of formula I:

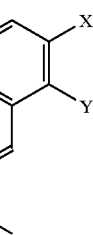

Formula I wherein $R_1$ is $C_1$ to $C_{12}$ alkyl which is optionally substituted by a $C_1$–$C_4$ alkoxyl, a trifluromethyl or $(C_6H_5CH_2)(CH_3)N$ and X and Y are independently selected from the group consisting of H, $C_1$ to $C_6$ alkyl, $C_1$ to $C_6$ alkoxy, $C_1$ to $C_6$ alkylaryl, halo, aryl, substituted aryl, and nitro, comprising the condensation of an aldehyde of formula II:

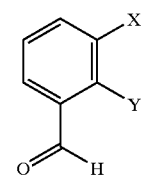

Formula II with an acetoacetate of formula III

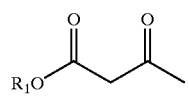

Formula III in the presence of a pyridyl carboxylic acid of formula IV

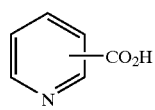

Formula IV and a secondary amine of formula V

HNR$_3$R$_4$  Formula V where $R_3$ and $R_4$ are independently $C_1$–$C_7$ alkyl or aralkyl, or a secondary amine of formula VI Formula VI

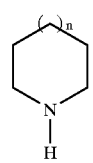

Formula VI wherein n=0, 1, 2, 3.

Additionally it is a further object of the invention to provide for the further reacting of the benzylidene intermediate of formula I with a substituted enamine of formula VII Formula VII

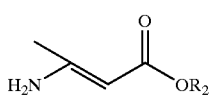

where $R_2$ is $C_1$ to $C_{12}$ alkyl which is optionally substituted by a $C_1$–$C_4$ alkoxyl, a trifluroromethyl or $(C_6H_5CH_2)(CH_3)N$ and $R_2$ is not the same as $R_1$ to form the dihydropyridine compound useful as a medicine of formula VIII Formula VIII

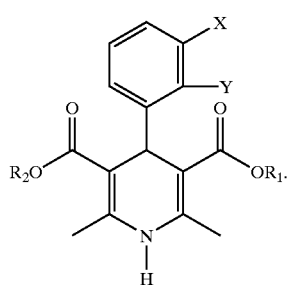

In one instance, the intermediates prepared can be used to obtain relatively high purity and yield of felodipine or nitrendipine with little additional purification steps.

One can prepare a benzylidene intermediate useful in the preparation of the medicine felodipine. Thus, 2,3-dichlorobenzaldehyde is condensed with methyl acetoacetate in the presence of a novel catalyst system forming the benzylidene intermediate, 4a

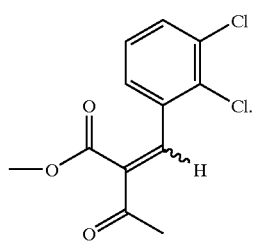

4a

This benzylidene intermediate prepared using the novel catalyst system can further be reacted with ethyl aminocrotonate to provide felodipine.

In another instance, the process to prepare a nitrendipine benzylidene intermediate follows a similar process except that 3-nitrobenzaldehyde is used instead of 2,3-dichlorobenzaldehyde.

Surprisingly and unexpectedly, we have discovered that the resulting dihydropyridine, for example felodipine could be isolated in very high purity (>99.5%) directly from the reaction mixture if the benzylidene intermediate 4 could be isolated in highly pure form (>99%). In another aspect of the present invention, we have found a novel catalyst system through which the benzylidene intermediate could be prepared in high purity and high yield.

Thus, 2,3-dichlorobenzaldehyde reacts with methyl acetoacetate in the presence of a catalytic amount of pyridyl carboxylic acid and piperidine in an alcoholic solvent at a temperature of 30–60° C. for 5–10 hours. After cooling to 10–40° C., the reaction mixture is maintained for a period of 3–10 hours. The resulting solid is filtered and washed with alcohol solvent (corrected yield 80–85%). The damp solid is used directly in the next step. In the second step, the benzylidene intermediate reacts with ethyl aminocrotonate in an alcoholic solvent under reflux temperature for 10–30 hours. The solvent is removed and an anti-solvent is added. The product is then filtered and washed with an additional amount of solvent thereby furnishing felodipine in a yield of about 80–95% from the benzylidene intermediate and a HPLC purity of 99.6%. Furthermore, the product meets the high purity specifications required for pharmaceutical active ingredients without necessitating the need for further purification.

DETAILED DESCRIPTION OF THE INVENTION

One aspect of the invention relates to the convenient preparation of intermediates useful in the preparation of dihydropyridines useful as medicines, for example, felodipine. This invention also covers the generic preparation of other intermediate for similar members of the dipine class of antihypertensives and muscle relaxants. Examples that this invention is applicable to include, but is not limited to, dihydropyridines such as nitrendipine, nisoldipine, nimodipine, nilvadipine, arandipine, lacidipine, manidipine, isradipine, amlodipine, cronidipine, diperdipine, and furaldipine. It is well understood by one skilled in the art that analogous procedures can be used to manufacture these dihydropyridines intermediates and the resulting dihydropyridine molecules.

The synthetic scheme depicted in Scheme 1 illustrates the reaction sequence for the preparation of felodipine using the intermediate formed by the process of the present invention. This scheme is for exemplary purposes and the application to other dihydropyridines such as those mentioned above will be readily apparent by one skilled in the art.

Step I

One embodiment of the present invention involves the synthesis of the intermediate methyl benzylidene 4a.

Surprisingly and unexpectedly, we have found that a catalytic system comprised of a pyridyl carboxylic acid, of formula IV (Scheme 3), in combination with a secondary amine, of formula V, or VI (Scheme 3), serves this purpose very well. The basic centre on the pyridine ring plays an unexpectedly important role in this system. Examples of the pyridyl carboxylic acid include picolinic acid, nicotinic acid and 4-pyridyl carboxylic acid, most preferably picolinic acid. Examples of secondary amine of formula V include amines where $R_3$ and $R_4$ are $C_1$–$C_7$ alkyl, aralkyl. Examples of secondary amines of formula VI include amines where n=0, 1, 2, and 3, most preferably piperidine. When systems such as this are employed as catalyst, the condensation reaction proceeds cleanly and the benzylidene intermediate precipitates out upon cooling and without distillation of the solvent.

Scheme 3

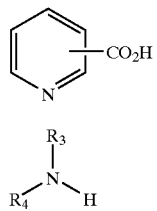

IV

V

-continued

VI

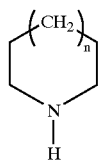

Also of importance, catalysts of the aforementioned type favour the equilibrium to the less soluble isomer relative to the more soluble isomer (Scheme 4) thereby permitting convenient isolation of the less soluble isomer by filtration and in high purity (>99% as a single isomer) and high yield (>80%). The advantages of being able to obtain the benzylidene in pure form will become apparent in the preparation of felodipine in step II and are demonstrated by comparing felodipine prepared in Example 1 versus Comparative Example 2.

Scheme 4

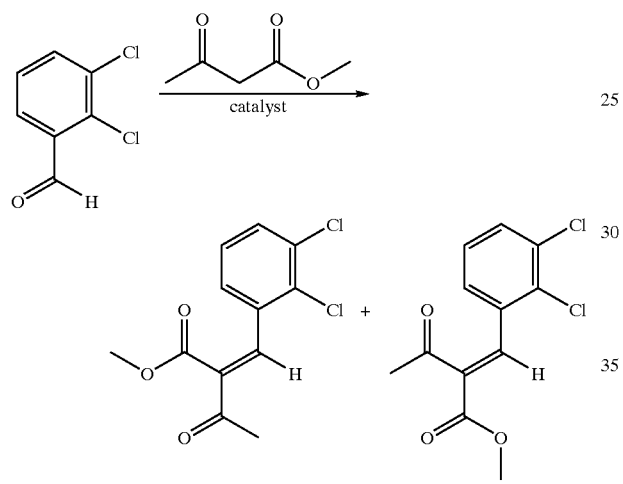

Step II

The benzylidene intermediate of step I is condensed with a suitable substituted enamine, such as ethyl aminocrotonate, in a refluxing alcoholic solvent, preferably isopropanol. In one embodiment of the present invention, the methyl benzylidene intermediate formed in step I is preferably isolated and reacted with ethyl aminocrotonate. Preferably the methyl benzylidene intermediate is suspended in isopropanol and ethyl aminocrotonate is added, and the contents refluxed until the reaction is completed.

Contrary to the teachings of the prior art and a clear advantage in this present invention, the felodipine reaction is not sensitive to the amount of ethyl aminocrotonate charged during the second step. The amount of ethyl aminocrotonate could be 0.8–2.0 equivalent of benzylidene, preferably 1.1–1.4 equivalents. We have found that if the benzylidene is clean (>99% as single isomer), the product could be isolated in high purity (>99.5%) and high yield (>87% based on benzylidene). The reaction could be run under reflux for 8–30 hours, preferably 15–20 hours, in an alcohol solvent, preferably isopropanol.

The product is isolated conveniently by removing a portion of the isopropanol and adding an anti-solvent, such as heptanes, and then filtration. The product is dried and is pharmaceutically acceptable without further purification.

The following examples are illustrative of the invention and are not to be considered limiting the scope of the invention in any manner.

EXAMPLES

Example 1

Preparation of Felodipine

Step I

To a solution of 2,3-dichlorobenzaldehyde (101.0 g, 0.58 mol) in isopropanol (450 mL) is added picolinic acid (3.5 g, 29 mmol), piperidine (2.4 g, 29 mmol) and methyl acetoacetate (86.3 g, 0.74 mol). The solution is stirred at 40–45° C. for 6 h, cooled to room temperature and the solid is filtered and washed with isopropanol. The damp cake is dried to yield 125.9 g (80%) benzylidene 4a as white solid.

Step II

To a suspension of benzylidene from step I (125.9 g, 0.46 mol) in isopropanol (600 mL) is added ethyl aminocrotonate (71.5 g, 0.55 mol). The reaction mixture is heated under reflux for 12 hours. Isopropanol is distilled and heptanes (400 mL) is added. The resulting solid is filtered and washed with heptanes. After drying 151.9 g (86%) felodipine is obtained as pale yellow solid with a purity of 99.6% (a/a). Melting range: 142–144° C. (corrected). $^1$H NMR (300 MHz, CDCl$_3$): δ=7.30 (1H, dd); 7.24 (1H, dd); 7.06 (1H, at); 5.84 (1H, s); 5.46 (1H, s); 4.07 (2H, q); 3.61 (3H, s); 2.31 (3H, s); 2.29 (3H, s); 1.18 (3H, t); $^{13}$C NMR (75 MHz, CDCl$_3$): δ=168.1; 167.6; 148.3; 144.5; 144.4; 132.9; 131.2; 129.9; 128.4; 127.2; 104.0; 103.6; 60.0; 51.1; 38.8; 19.7; 19.6; 14.5.

Comparative Example 2

Preparation of Felodipine Without Isolation of the Benzylidene Intermediate

To a solution of 2,3-dichlorobenzaldehyde (8.76 g, 0.05 mol) in isopropanol (80 mL) is added picolinic acid (0.65 g, 5.4 mmol), piperidine (0.45 g, 5.4 mmol) and methyl acetoacetate (86.3 g, 0.06 mol). The solution is stirred at 40–45° C. for 6 h, and then isopropanol is distilled under vacuum. The residue is dissolved in ethyl acetate (80 mL) and washed with water (60 mL). Ethyl acetate is then removed under vacuum. To the residue is added ethyl aminocrotonate (7.74 g, 0.06 mol) and isopropanol (60 mL). The mixture is heated under reflux for 4 hours. Isopropanol is distilled and heptanes (60 mL) is added. The resulting solid is filtered and washed with heptanes. After drying 12.7 g (66%) felodipine is obtained as pale yellow solid with a purity of 94.4% (diethyl and dimethyl have a concentration of 2.02% and 3.38% (a/a), respectively).

Example 3

Preparation of Nitrendipine

Step I

To a solution of 3-nitrobenzaldehyde (75.6 g, 0.50 mol) in isopropanol (250 mL) is added picolinic acid (4.74 g, 39 mmol), piperidine (3.54 g, 39 mmol) and methyl acetoacetate (75.4 g, 0.65 mol). The solution is stirred at 40–45° C. for 6 h, cooled to room temperature and the solid is filtered and washed with isopropanol. The damp cake is dried to yield 108.3 g (87%) benzylidene as pale yellow solid.

Step II

To a suspension of benzylidene (108.3 g, 0.43 mol) in isopropanol (400 mL) is added ethyl aminocrotonate (67.3 g, 0.52 mol). The reaction mixture is heated under reflux for 10 hours, cooled to room temperature and the solid is filtered and washed with isopropanol. After drying 140.1 g (89%) nitrendipine is obtained as pale yellow solid.

¹H NMR (300 MHz, DMSO-d₆): δ=9.06 (1H, s); 8.05–7.97 (2H, m); 7.66–7.52 (2H, m); 4.99 (1H, s); 4.04 (2H, q); 3.55 (3H, s); 2.31 (3H, s); 2.30 (3H, s); 1.15 (3H, t); ¹³C NMR (75 MHz, DMSO-D₆): δ=167.0; 166.5; 150.1; 147.6; 146.6; 146.4; 134.1; 129.6; 121.7; 121.1; 101.1; 100.8; 59.2; 50.8; 39.1; 18.3; 18.2; 14.1.

What is claimed is:

1. A process for the manufacture of a benzylidene intermediate of formula

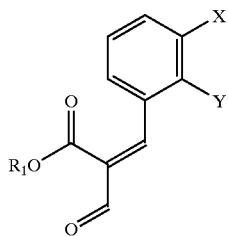

wherein R₁ is C₁ to C₁₂ alkyl which is optionally substituted by a C₁–C₄ alkoxyl, a triflurorormethyl or (C₆H₅CH₂)(CH₃)N and X and Y are independently selected from the group consisting of H, C₁ to C₆ alkyl, C₁ to C₆ alkoxy, C₁ to C₆ alkylaryl, halo, aryl, substituted aryl, and nitro, comprising the condensation reaction of an aldehyde of formula

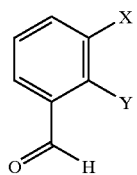

with an acetoacetate of formula

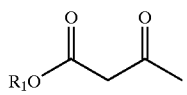

in the presence of catalytic amounts of a pyridyl carboxylic acid of formula

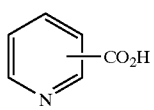

and a secondary amine.

2. The process of claim 1 wherein the secondary amine is of formula where R₃ and R₄ are independently C₁–C₇ alkyl or aralkyl.

3. The process of claim 1 wherein the secondary amine is of formula

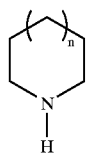

where n=0, 1, 2, 3.

4. The process of claim 1 wherein the secondary amine is piperidine.

5. The process of claim 1 wherein the pyridyl carboxylic acid is picolinic acid.

6. The process of any of claims 1 to 5 further comprising the reaction of said benzylidene intermediate with a substituted enamine of formula

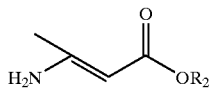

where R₂ is C₁ to C₁₂ alkyl which is optionally substituted by a C₁–C₄ alkoxyl, a trifluoromethyl or (C₆H₅CH₂)(CH₃)N and R₂ is not the same as R₁ wherein the dihydropyridine compound of formula

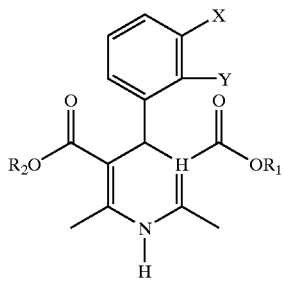

is formed.

7. A process for the preparation of a benzylidene intermediate of any of claims 1, 2, 3, 4 or 5 wherein X=Cl, Y=Cl and R₁ is selected from the group consisting of methyl or ethyl.

8. A process for the preparation of a benzylidene intermediate of any of claims 1, 2, 3, 4 or 5 wherein X=NO₂, Y=H and R₁ is selected from the group consisting of methyl or ethyl.

9. A process for the preparation of felodipine comprising:
(a) the condensation reaction of an aldehyde of formula

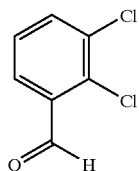

with an acetoacetate of formula

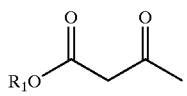

in the presence of catalytic amounts of a pyridyl carboxylic acid of formula

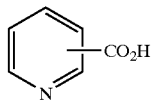

and a secondary amine; and
(b) the reaction of the resulting product with an enamine of formula

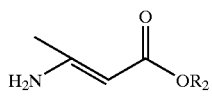

wherein $R_1$ and $R_2$ are methyl and ethyl respectively or ethyl and methyl respectively.

10. The process of claim 9 wherein the secondary amine is of formula

wherein $R_3$ and $R_4$ are each independently $C_1$–$C_7$ alkyl or aralkyl.

11. The process of claim 9 wherein the secondary amine is of formula

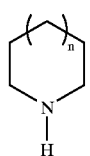

where n=0, 1, 2 or 3.

12. The process of claim 9 wherein the secondary amine is piperidine.

13. The process of claim 9 wherein the pyridyl carboxylic acid is picolinic acid.

14. A process for the preparation of nitrendipine comprising:

(a) the condensation reaction of an aldehyde of formula

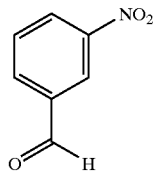

with an acetoacetate of formula

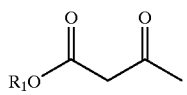

in the presence of catalytic amounts of a pyridyl carboxylic acid of formula

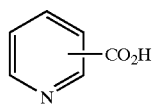

and a secondary amine; and (b) the reaction of the resulting product with an enamine of formula

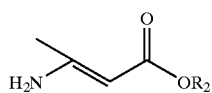

wherein $R_1$ and $R_2$ are methyl and ethyl respectively or ethyl and methyl respectively.

15. The process of claim 14 wherein the secondary amine is of formula

wherein $R_3$ and $R_4$ are each independently $C_1$–$C_7$ alkyl or aralkyl.

16. The process of claim 14 wherein the secondary amine is of formula

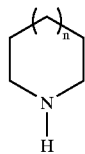

where n=0, 1, 2 or 3.

17. The process of claim 14 wherein the secondary amine is piperidine.

18. The process of claim 14 wherein the pyridyl carboxylic acid is picolinic acid.

19. The process of any of claims 1, 9 or 14 wherein one of the reactions is performed in at least one alcoholic solvent.

20. The process of claim 19 wherein the alcoholic solvent is isopropanol.

21. The process of claim 6 wherein the benzylamidine intermediate is isolated prior to the reaction with the enamine.

* * * * *

UNITED STATES PATENT AND TRADEMARK OFFICE
CERTIFICATE OF CORRECTION

PATENT NO.    : 6,858,747 B2
DATED         : February 22, 2005
INVENTOR(S)   : Daqing Che, Bhaskar Reddy Guntoori and S. Keshava Murthy It is certified that error appears in the above-identified patent and that said Letters Patent is hereby corrected as shown below:

Column 9,
Line 52, cancel the text beginning with "2. The process of claim 1" to and ending with "alkyl or aralkyl." and insert the following claim:

2. The process of claim 1 wherein the secondary amine is of formula $$HNR_3R_4$$

where $R_3$ and $R_4$ are independently $C_1$-$C_7$ alkyl or aralkyl.

Signed and Sealed this

Sixth Day of December, 2005

JON W. DUDAS
*Director of the United States Patent and Trademark Office*